(12) United States Patent
Kusleika

(10) Patent No.: US 9,561,122 B2
(45) Date of Patent: Feb. 7, 2017

(54) VASCULAR DEVICE FOR ANEURYSM TREATMENT AND PROVIDING BLOOD FLOW INTO A PERFORATOR VESSEL

(71) Applicant: Covidien LP, Mansfield, MA (US)

(72) Inventor: Richard Kusleika, Excelsior, MN (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/875,732

(22) Filed: Oct. 6, 2015

(65) Prior Publication Data

US 2016/0022451 A1    Jan. 28, 2016

Related U.S. Application Data

(63) Continuation of application No. 13/826,147, filed on Mar. 14, 2013, now Pat. No. 9,157,174.

(Continued)

(51) Int. Cl.
  *A61F 2/90* (2013.01)
  *D04C 1/02* (2006.01)
  (Continued)

(52) U.S. Cl.
  CPC ........... *A61F 2/90* (2013.01); *A61B 17/12036* (2013.01); *A61B 17/12109* (2013.01); *A61B 17/12113* (2013.01); *A61B 17/12172* (2013.01); *A61F 2/844* (2013.01); *A61F 2/856* (2013.01); *D04C 1/02* (2013.01); *D04C 1/06* (2013.01);
  (Continued)

(58) Field of Classification Search
  CPC ................ A61F 2/04; A61F 2/06; A61F 2/82; A61F 2/844; A61F 2/86; A61F 2/90; A61F 2002/068; A61F 2002/823;A61B 17/12036; A61B 17/12113; A61B 17/12172
  See application file for complete search history.

(56) References Cited

U.S. PATENT DOCUMENTS 2,919,467 A    1/1960    Mercer
4,321,711 A    3/1982    Mano
(Continued)

FOREIGN PATENT DOCUMENTS

CN    101472537 A    7/2009
EP      855170 A2    7/1998
(Continued)

OTHER PUBLICATIONS

Benndorf, et al. Treatment of a Ruptured Dissecting Vertebral Artery Aneurysm with Double Stent Placement: Case Report AJNR Am J Neuroradiol, Nov.-Dec. 2001, vol. 22, pp. 1844-1848.

(Continued)

*Primary Examiner* — David Isabella
*Assistant Examiner* — Dinah Baria
(74) *Attorney, Agent, or Firm* — Mark J. Kertz, Esq.

(57) ABSTRACT

A vascular device includes a body having a first, collapsed configuration and a second, expanded configuration. The body includes a plurality of heat-set strands that are braided such that when the body is in the second configuration, the strands form a plurality of pores and one or more apertures between the strands. The apertures are generally disposed at a longitudinal center region of the body. When the body is in the second configuration, the pores at proximal and distal portions of the body are generally uniform in size and smaller in size than the apertures. The pores and the apertures are substantially the same size when the body is in the first configuration.

20 Claims, 5 Drawing Sheets

Related U.S. Application Data

(60) Provisional application No. 61/760,907, filed on Feb. 5, 2013.

(51) Int. Cl.

| | | |
|---|---|---|
| *D04C 1/06* | (2006.01) | |
| *A61B 17/12* | (2006.01) | |
| *A61F 2/856* | (2013.01) | |
| *A61F 2/844* | (2013.01) | |
| *A61F 2/86* | (2013.01) | |
| *A61B 17/00* | (2006.01) | |
| *A61F 2/82* | (2013.01) | |

(52) U.S. Cl.
CPC ............ *A61B 2017/00526* (2013.01); *A61B 2017/00867* (2013.01); *A61B 2017/1205* (2013.01); *A61F 2/86* (2013.01); *A61F 2002/823* (2013.01)

(56) References Cited

U.S. PATENT DOCUMENTS

| | | |
|---|---|---|
| 4,503,569 A | 3/1985 | Dotter |
| 4,512,338 A | 4/1985 | Balko et al. |
| 4,538,622 A | 9/1985 | Samson et al. |
| 4,572,186 A | 2/1986 | Gould et al. |
| 4,580,568 A | 4/1986 | Gianturco |
| 4,655,771 A | 4/1987 | Wallsten |
| 4,681,110 A | 7/1987 | Wiktor |
| 4,733,665 A | 3/1988 | Palmaz |
| 4,743,251 A | 5/1988 | Barra |
| 4,768,507 A | 9/1988 | Fischell et al. |
| 4,776,337 A | 10/1988 | Palmaz |
| 4,856,516 A | 8/1989 | Hillstead |
| 4,954,126 A | 9/1990 | Wallsten |
| 5,011,488 A | 4/1991 | Ginsburg |
| 5,035,706 A | 7/1991 | Giantureo et al. |
| 5,041,126 A | 8/1991 | Gianturco |
| 5,061,275 A | 10/1991 | Wallsten et al. |
| 5,108,416 A | 4/1992 | Ryan et al. |
| 5,160,341 A | 11/1992 | Brenneman et al. |
| 5,180,368 A | 1/1993 | Garrison |
| 5,192,297 A | 3/1993 | Hull |
| 5,197,978 A | 3/1993 | Hess |
| 5,201,757 A | 4/1993 | Heyn et al. |
| 5,209,731 A | 5/1993 | Sterman et al. |
| 5,242,399 A | 9/1993 | Lau et al. |
| 5,246,420 A | 9/1993 | Kraus et al. |
| 5,246,445 A | 9/1993 | Yachia et al. |
| 5,330,500 A | 7/1994 | Song |
| 5,344,426 A | 9/1994 | Lau et al. |
| 5,360,443 A | 11/1994 | Barone et al. |
| 5,382,259 A | 1/1995 | Phelps et al. |
| 5,401,257 A | 3/1995 | Chevalier, Jr. et al. |
| 5,405,377 A | 4/1995 | Cragg |
| 5,405,380 A | 4/1995 | Gianotti et al. |
| 5,415,637 A | 5/1995 | Khosravi |
| 5,421,826 A | 6/1995 | Crocker et al. |
| 5,423,849 A | 6/1995 | Engelson et al. |
| 5,449,372 A | 9/1995 | Schmaltz et al. |
| 5,458,615 A | 10/1995 | Klemm et al. |
| 5,476,505 A | 12/1995 | Limon |
| 5,480,423 A | 1/1996 | Ravenscroft et al. |
| 5,484,444 A | 1/1996 | Braunschweiler |
| 5,489,295 A | 2/1996 | Piplani et al. |
| 5,507,767 A | 4/1996 | Maeda et al. |
| 5,507,768 A | 4/1996 | Lau et al. |
| 5,522,822 A | 6/1996 | Phelps et al. |
| 5,534,007 A | 7/1996 | St. Germain et al. |
| 5,545,208 A | 8/1996 | Wolff et al. |
| 5,546,880 A | 8/1996 | Ronyak et al. |
| 5,549,662 A | 8/1996 | Fordenbacher |
| 5,562,641 A | 10/1996 | Flomenblit et al. |
| 5,562,728 A | 10/1996 | Lazarus et al. |
| 5,591,225 A | 1/1997 | Okuda |
| 5,599,291 A | 2/1997 | Balbierz et al. |
| 5,601,593 A | 2/1997 | Freitag |
| 5,607,466 A | 3/1997 | Imbert et al. |
| 5,609,625 A | 3/1997 | Piplani et al. |
| 5,626,602 A | 5/1997 | Gianotti et al. |
| 5,628,783 A | 5/1997 | Quiachon et al. |
| 5,628,788 A | 5/1997 | Pinchuk |
| 5,632,771 A | 5/1997 | Boatman et al. |
| 5,632,772 A | 5/1997 | Alcime et al. |
| 5,636,641 A | 6/1997 | Fariabi |
| 5,637,113 A | 6/1997 | Tartaglia et al. |
| 5,639,278 A | 6/1997 | Dereume et al. |
| 5,645,559 A | 7/1997 | Hachtman et al. |
| D381,932 S | 8/1997 | Walshe et al. |
| 5,667,522 A | 9/1997 | Flomenblit et al. |
| 5,674,276 A | 10/1997 | Andersen et al. |
| 5,683,451 A | 11/1997 | Lenker et al. |
| 5,690,120 A | 11/1997 | Jacobsen |
| 5,690,644 A | 11/1997 | Yurek et al. |
| 5,695,499 A | 12/1997 | Helgerson et al. |
| 5,700,269 A | 12/1997 | Pinchuk et al. |
| 5,702,418 A | 12/1997 | Ravenscroft |
| 5,709,702 A | 1/1998 | Cogita |
| 5,709,703 A | 1/1998 | Lukic et al. |
| 5,718,159 A | 2/1998 | Thompson |
| 5,725,570 A | 3/1998 | Heath |
| 5,733,327 A | 3/1998 | Igaki et al. |
| 5,735,859 A | 4/1998 | Fischell et al. |
| 5,741,325 A | 4/1998 | Chaikof et al. |
| 5,741,333 A | 4/1998 | Frid |
| 5,746,765 A | 5/1998 | Kleshinski et al. |
| 5,749,883 A | 5/1998 | Halpern |
| 5,749,920 A | 5/1998 | Quiachon et al. |
| 5,769,884 A | 6/1998 | Solovay |
| 5,769,885 A | 6/1998 | Quiachon et al. |
| 5,776,099 A | 7/1998 | Tremulis |
| 5,776,142 A | 7/1998 | Gunderson |
| 5,782,909 A | 7/1998 | Quiachon et al. |
| 5,797,952 A | 8/1998 | Klein |
| 5,800,518 A | 9/1998 | Piplani et al. |
| 5,810,837 A | 9/1998 | Hofmann et al. |
| 5,817,102 A | 10/1998 | Johnson et al. |
| 5,817,105 A | 10/1998 | Van Der Brug |
| 5,824,039 A | 10/1998 | Piplani et al. |
| 5,824,041 A | 10/1998 | Lenker et al. |
| 5,824,042 A | 10/1998 | Lombardi et al. |
| 5,824,044 A | 10/1998 | Quiachon et al. |
| 5,824,058 A | 10/1998 | Ravenscroft et al. |
| 5,830,229 A | 11/1998 | Konya et al. |
| 5,833,632 A | 11/1998 | Jacobsen et al. |
| 5,836,868 A | 11/1998 | Ressemann et al. |
| 5,843,168 A | 12/1998 | Dang |
| 5,868,754 A | 2/1999 | Levine et al. |
| 5,876,419 A | 3/1999 | Carpenter et al. |
| 5,876,445 A | 3/1999 | Andersen |
| 5,888,201 A | 3/1999 | Stinson et al. |
| 5,902,266 A | 5/1999 | Leone et al. |
| 5,902,317 A | 5/1999 | Kleshinski et al. |
| 5,906,640 A | 5/1999 | Penn et al. |
| 5,911,717 A | 6/1999 | Jacobsen et al. |
| 5,916,194 A | 6/1999 | Jacobsen et al. |
| 5,919,204 A | 7/1999 | Lukic et al. |
| 5,928,260 A | 7/1999 | Chin et al. |
| 5,944,728 A | 8/1999 | Bates |
| 5,951,599 A | 9/1999 | McCrory |
| 5,957,973 A | 9/1999 | Quiachon et al. |
| 5,957,974 A | 9/1999 | Thompson et al. |
| 5,964,797 A | 10/1999 | Ho |
| 5,980,530 A | 11/1999 | Willard |
| 5,980,533 A | 11/1999 | Holman |
| 5,984,957 A | 11/1999 | Laptewicz, Jr. et al. |
| 6,012,277 A | 1/2000 | Prins et al. |
| 6,014,919 A | 1/2000 | Jacobsen et al. |
| 6,015,432 A | 1/2000 | Rakos et al. |
| 6,017,319 A | 1/2000 | Jacobsen et al. |
| 6,019,778 A | 2/2000 | Wilson et al. |
| 6,019,786 A | 2/2000 | Thompson |
| 6,022,369 A | 2/2000 | Jacobsen et al. |
| 6,024,754 A | 2/2000 | Engelson |

(56) References Cited

U.S. PATENT DOCUMENTS

| | | |
|---|---|---|
| 6,024,763 A | 2/2000 | Lenker et al. |
| 6,027,516 A | 2/2000 | Kolobow et al. |
| 6,033,436 A | 3/2000 | Steinke et al. |
| 6,039,721 A | 3/2000 | Johnson |
| 6,039,758 A | 3/2000 | Quiachon et al. |
| 6,042,589 A | 3/2000 | Marianne |
| 6,051,021 A | 4/2000 | Frid |
| 6,056,993 A | 5/2000 | Leidner et al. |
| 6,063,111 A | 5/2000 | Hieshima et al. |
| 6,074,407 A | 6/2000 | Levine et al. |
| 6,077,295 A | 6/2000 | Limon et al. |
| 6,080,191 A | 6/2000 | Summers |
| 6,083,257 A | 7/2000 | Taylor et al. |
| 6,093,199 A | 7/2000 | Brown et al. |
| 6,096,052 A | 8/2000 | Callister et al. |
| 6,102,942 A | 8/2000 | Ahari |
| 6,123,712 A | 9/2000 | Di Caprio et al. |
| 6,126,685 A | 10/2000 | Lenker et al. |
| 6,132,459 A | 10/2000 | Piplani et al. |
| 6,139,543 A | 10/2000 | Esch et al. |
| 6,146,415 A | 11/2000 | Fitz |
| 6,149,680 A | 11/2000 | Shelso et al. |
| 6,159,228 A | 12/2000 | Frid et al. |
| 6,161,399 A | 12/2000 | Jayaraman |
| 6,165,194 A | 12/2000 | Denardo |
| 6,165,210 A | 12/2000 | Lau et al. |
| 6,165,213 A | 12/2000 | Goicoechea et al. |
| 6,168,592 B1 | 1/2001 | Kupiecki et al. |
| 6,174,330 B1 | 1/2001 | Stinson |
| 6,183,410 B1 | 2/2001 | Jacobsen et al. |
| 6,183,508 B1 | 2/2001 | Stinson et al. |
| 6,187,013 B1 | 2/2001 | Stoltze et al. |
| 6,193,708 B1 | 2/2001 | Ken et al. |
| 6,197,046 B1 | 3/2001 | Piplani et al. |
| 6,203,569 B1 | 3/2001 | Wijay |
| 6,206,868 B1 | 3/2001 | Parodi |
| 6,210,400 B1 | 4/2001 | Hebert et al. |
| 6,210,434 B1 | 4/2001 | Quiachon et al. |
| 6,210,435 B1 | 4/2001 | Piplani et al. |
| 6,214,038 B1 | 4/2001 | Piplani et al. |
| 6,214,042 B1 | 4/2001 | Jacobsen et al. |
| 6,221,102 B1 | 4/2001 | Baker et al. |
| 6,224,609 B1 | 5/2001 | Ressemann et al. |
| 6,224,829 B1 | 5/2001 | Piplani et al. |
| 6,231,598 B1 | 5/2001 | Berry et al. |
| 6,235,050 B1 | 5/2001 | Quiachon et al. |
| 6,241,759 B1 | 6/2001 | Piplani et al. |
| 6,245,087 B1 | 6/2001 | Addis |
| 6,245,103 B1 | 6/2001 | Stinson |
| 6,251,132 B1 | 6/2001 | Ravenscroft et al. |
| 6,258,115 B1 | 7/2001 | Dubrul |
| 6,260,458 B1 | 7/2001 | Jacobsen et al. |
| 6,261,305 B1 | 7/2001 | Marotta et al. |
| 6,261,316 B1 | 7/2001 | Shaolian et al. |
| 6,264,671 B1 | 7/2001 | Stack et al. |
| 6,264,689 B1 | 7/2001 | Colgan et al. |
| 6,270,523 B1 | 8/2001 | Herweck et al. |
| 6,280,465 B1 | 8/2001 | Cryer |
| 6,283,991 B1 | 9/2001 | Cox et al. |
| 6,287,331 B1 | 9/2001 | Heath |
| 6,287,333 B1 | 9/2001 | Appling et al. |
| 6,290,721 B1 | 9/2001 | Heath |
| 6,299,636 B1 | 10/2001 | Schmitt et al. |
| 6,302,810 B2 | 10/2001 | Yokota |
| 6,302,893 B1 | 10/2001 | Limon et al. |
| 6,309,353 B1 | 10/2001 | Cheng et al. |
| 6,322,576 B1 | 11/2001 | Wallace et al. |
| 6,322,586 B1 | 11/2001 | Monroe et al. |
| 6,322,587 B1 | 11/2001 | Quiachon et al. |
| 6,325,826 B1 | 12/2001 | Vardi et al. |
| 6,334,871 B1 | 1/2002 | Dor et al. |
| 6,336,938 B1 | 1/2002 | Kavteladze et al. |
| 6,340,367 B1 | 1/2002 | Stinson et al. |
| 6,340,368 B1 | 1/2002 | Verbeck |
| 6,342,068 B1 | 1/2002 | Thompson |
| 6,344,041 B1 | 2/2002 | Kupiecki et al. |
| 6,348,063 B1 | 2/2002 | Yassour et al. |
| 6,350,199 B1 | 2/2002 | Williams et al. |
| 6,350,278 B1 | 2/2002 | Lenker et al. |
| 6,355,051 B1 | 3/2002 | Sisskind et al. |
| 6,355,061 B1 | 3/2002 | Quiachon |
| 6,364,895 B1 | 4/2002 | Greenhalgh |
| 6,368,339 B1 | 4/2002 | Amplatz |
| 6,368,344 B1 | 4/2002 | Fitz |
| 6,368,557 B1 | 4/2002 | Piplani et al. |
| 6,375,670 B1 | 4/2002 | Greenhalgh |
| 6,375,676 B1 | 4/2002 | Cox |
| 6,379,618 B1 | 4/2002 | Piplani et al. |
| 6,380,457 B1 | 4/2002 | Yurek et al. |
| 6,389,946 B1 | 5/2002 | Frid |
| 6,395,017 B1 | 5/2002 | Dwyer et al. |
| 6,395,021 B1 | 5/2002 | Hart et al. |
| 6,395,022 B1 | 5/2002 | Piplani et al. |
| 6,398,802 B1 | 6/2002 | Yee |
| 6,409,683 B1 | 6/2002 | Fonseca et al. |
| 6,413,235 B1 | 7/2002 | Parodi |
| 6,416,519 B1 | 7/2002 | VanDusseldorp |
| 6,416,536 B1 | 7/2002 | Yee |
| 6,419,693 B1 | 7/2002 | Fariabi |
| 6,428,489 B1 | 8/2002 | Jacobsen et al. |
| 6,440,088 B1 | 8/2002 | Jacobsen et al. |
| 6,443,971 B1 | 9/2002 | Boylan et al. |
| 6,443,979 B1 | 9/2002 | Stalker |
| 6,454,999 B1 | 9/2002 | Farhangnia et al. |
| 6,468,301 B1 | 10/2002 | Amplatz et al. |
| 6,477,768 B1 | 11/2002 | Wildner |
| 6,478,778 B1 | 11/2002 | Jacobsen et al. |
| 6,482,221 B1 | 11/2002 | Hebert et al. |
| 6,488,705 B2 | 12/2002 | Schmitt et al. |
| 6,491,648 B1 | 12/2002 | Cornish et al. |
| 6,494,895 B2 | 12/2002 | Addis |
| 6,497,711 B1 | 12/2002 | Plaia et al. |
| 6,503,450 B1 | 1/2003 | Afzal |
| 6,514,261 B1 | 2/2003 | Randall et al. |
| 6,514,285 B1 | 2/2003 | Pinchasik |
| 6,524,299 B1 | 2/2003 | Tran et al. |
| 6,527,763 B2 | 3/2003 | Esch et al. |
| 6,533,811 B1 | 3/2003 | Ryan et al. |
| 6,540,778 B1 | 4/2003 | Quiachon et al. |
| 6,547,779 B2 | 4/2003 | Levine |
| 6,551,352 B2 | 4/2003 | Clerc et al. |
| 6,572,646 B1 | 6/2003 | Boylan et al. |
| 6,576,006 B2 | 6/2003 | Limon et al. |
| 6,582,460 B1 | 6/2003 | Cryer |
| 6,582,461 B1 | 6/2003 | Burmeister et al. |
| 6,589,273 B1 | 7/2003 | McDermott |
| 6,592,616 B1 | 7/2003 | Stack et al. |
| 6,595,989 B1 | 7/2003 | Schaer |
| 6,602,271 B2 | 8/2003 | Adams et al. |
| 6,602,280 B2 | 8/2003 | Chobotov |
| 6,605,110 B2 | 8/2003 | Harrison |
| 6,613,075 B1 | 9/2003 | Healy et al. |
| 6,613,078 B1 | 9/2003 | Barone |
| 6,622,604 B1 | 9/2003 | Chouinard et al. |
| 6,623,518 B2 | 9/2003 | Thompson et al. |
| 6,635,068 B1 | 10/2003 | Dubrul et al. |
| 6,638,243 B2 | 10/2003 | Kupiecki |
| 6,645,240 B2 | 11/2003 | Yee |
| 6,646,218 B1 | 11/2003 | Campbell et al. |
| 6,652,508 B2 | 11/2003 | Griffin |
| 6,652,574 B1 | 11/2003 | Jayaraman |
| 6,656,212 B2 | 12/2003 | Ravenscroft et al. |
| 6,656,218 B1 | 12/2003 | Denardo et al. |
| 6,660,024 B1 | 12/2003 | Flaherty |
| 6,660,032 B2 | 12/2003 | Klumb et al. |
| 6,663,666 B1 | 12/2003 | Quiachon et al. |
| 6,666,881 B1 | 12/2003 | Richter et al. |
| 6,669,719 B2 | 12/2003 | Wallace |
| 6,673,089 B1 | 1/2004 | Yassour et al. |
| 6,673,100 B2 | 1/2004 | Diaz et al. |
| 6,679,893 B1 | 1/2004 | Tran |
| 6,682,557 B1 | 1/2004 | Quiachon et al. |
| 6,685,735 B1 | 2/2004 | Ahari |
| 6,689,120 B1 | 2/2004 | Gerdts |

(56) References Cited

U.S. PATENT DOCUMENTS

| | | |
|---|---|---|
| 6,689,162 B1 | 2/2004 | Thompson |
| 6,699,274 B2 | 3/2004 | Stinson |
| 6,702,843 B1 | 3/2004 | Brown et al. |
| 6,709,454 B1 | 3/2004 | Cox et al. |
| 6,712,834 B2 | 3/2004 | Yassour et al. |
| 6,726,700 B1 | 4/2004 | Levine |
| 6,733,519 B2 | 5/2004 | Lashinski et al. |
| 6,740,105 B2 | 5/2004 | Yodfat et al. |
| 6,740,112 B2 | 5/2004 | Yodfat et al. |
| 6,743,219 B1 | 6/2004 | Dwyer et al. |
| 6,755,855 B2 | 6/2004 | Yurek et al. |
| 6,758,885 B2 | 7/2004 | Leffel et al. |
| 6,767,361 B2 | 7/2004 | Quiachon et al. |
| 6,773,446 B1 | 8/2004 | Dwyer et al. |
| 6,793,667 B2 | 9/2004 | Hebert et al. |
| 6,814,746 B2 | 11/2004 | Thompson et al. |
| 6,814,748 B1 | 11/2004 | Baker et al. |
| 6,818,006 B2 | 11/2004 | Douk et al. |
| 6,833,003 B2 | 12/2004 | Jones et al. |
| 6,849,084 B2 | 2/2005 | Rabkin et al. |
| 6,858,034 B1 | 2/2005 | Hijlkema et al. |
| 6,860,893 B2 | 3/2005 | Wallace et al. |
| 6,860,898 B2 | 3/2005 | Stack et al. |
| 6,860,899 B1 | 3/2005 | Rivelli, Jr. |
| 6,860,900 B2 | 3/2005 | Clerc et al. |
| 6,860,901 B1 | 3/2005 | Baker et al. |
| 6,866,677 B2 | 3/2005 | Douk et al. |
| 6,866,679 B2 | 3/2005 | Kusleika |
| 6,866,680 B2 | 3/2005 | Yassour et al. |
| 6,881,221 B2 | 4/2005 | Golds |
| 6,887,267 B2 | 5/2005 | Dworschak et al. |
| 6,890,337 B2 | 5/2005 | Feeser et al. |
| 6,893,451 B2 | 5/2005 | Cano et al. |
| 6,918,921 B2 | 7/2005 | Brady et al. |
| 6,932,837 B2 | 8/2005 | Amplatz et al. |
| 6,936,055 B1 | 8/2005 | Ken et al. |
| 6,955,685 B2 | 10/2005 | Escamilla et al. |
| 6,960,227 B2 | 11/2005 | Jones et al. |
| 6,964,670 B1 | 11/2005 | Shah et al. |
| 6,964,672 B2 | 11/2005 | Brady et al. |
| 6,969,396 B2 | 11/2005 | Krolik et al. |
| 6,976,991 B2 | 12/2005 | Hebert et al. |
| 6,989,024 B2 | 1/2006 | Hebert et al. |
| 6,994,721 B2 | 2/2006 | Israel |
| 7,001,422 B2 | 2/2006 | Escamilla et al. |
| 7,004,962 B2 | 2/2006 | Stinson |
| 7,004,964 B2 | 2/2006 | Thompson et al. |
| 7,011,675 B2 | 3/2006 | Hemerick et al. |
| 7,037,330 B1 | 5/2006 | Rivelli, Jr. et al. |
| 7,041,129 B2 | 5/2006 | Rourke et al. |
| 7,066,951 B2 | 6/2006 | Chobotov |
| 7,069,835 B2 | 7/2006 | Nishri et al. |
| 7,074,236 B2 | 7/2006 | Rabkin et al. |
| 7,093,527 B2 | 8/2006 | Rapaport et al. |
| 7,101,392 B2 | 9/2006 | Heath |
| 7,107,105 B2 | 9/2006 | Bjorklund et al. |
| 7,118,539 B2 | 10/2006 | Vrba et al. |
| 7,118,594 B2 | 10/2006 | Quiachon et al. |
| 7,122,050 B2 | 10/2006 | Randall et al. |
| 7,137,990 B2 | 11/2006 | Hebert et al. |
| 7,166,125 B1 | 1/2007 | Baker et al. |
| 7,169,170 B2 | 1/2007 | Widenhouse |
| 7,169,172 B2 | 1/2007 | Levine et al. |
| 7,172,617 B2 | 2/2007 | Colgan et al. |
| 7,192,434 B2 | 3/2007 | Anderson et al. |
| 7,195,639 B2 | 3/2007 | Quiachon et al. |
| 7,195,648 B2 | 3/2007 | Jones et al. |
| 7,201,768 B2 | 4/2007 | Diaz et al. |
| 7,201,769 B2 | 4/2007 | Jones et al. |
| 7,211,109 B2 | 5/2007 | Thompson |
| 7,213,495 B2 | 5/2007 | McCullagh et al. |
| 7,220,271 B2 | 5/2007 | Clubb et al. |
| 7,235,096 B1 | 6/2007 | Van Tassel et al. |
| 7,264,632 B2 | 9/2007 | Wright et al. |
| 7,275,471 B2 | 10/2007 | Nishri et al. |
| 7,279,005 B2 | 10/2007 | Stinson |
| 7,279,208 B1 | 10/2007 | Goffena et al. |
| 7,294,137 B2 | 11/2007 | Rivelli, Jr. et al. |
| 7,294,146 B2 | 11/2007 | Chew et al. |
| 7,300,456 B2 | 11/2007 | Andreas et al. |
| 7,300,460 B2 | 11/2007 | Levine et al. |
| 7,306,624 B2 | 12/2007 | Yodfat et al. |
| 7,309,351 B2 | 12/2007 | Escamilla et al. |
| 7,311,031 B2 | 12/2007 | McCullagh et al. |
| 7,320,702 B2 | 1/2008 | Hammersmark et al. |
| 7,323,001 B2 | 1/2008 | Clubb et al. |
| 7,331,973 B2 | 2/2008 | Gesswein et al. |
| 7,331,976 B2 | 2/2008 | McGuckin, Jr. et al. |
| 7,331,985 B2 | 2/2008 | Thompson et al. |
| 7,338,518 B2 | 3/2008 | Chobotov |
| 7,438,712 B2 | 10/2008 | Chouinard |
| 7,462,192 B2 | 12/2008 | Norton et al. |
| 7,468,070 B2 | 12/2008 | Henry et al. |
| 7,470,282 B2 | 12/2008 | Shelso |
| 7,473,271 B2 | 1/2009 | Gunderson |
| 7,491,224 B2 | 2/2009 | Cox et al. |
| 7,520,893 B2 | 4/2009 | Rivelli, Jr. |
| RE40,816 E | 6/2009 | Taylor et al. |
| 7,572,288 B2 | 8/2009 | Cox |
| 7,572,290 B2 | 8/2009 | Yodfat et al. |
| 7,588,597 B2 | 9/2009 | Frid |
| 7,695,507 B2 | 4/2010 | Rivelli, Jr. et al. |
| 7,763,011 B2 | 7/2010 | Ortiz et al. |
| 7,771,463 B2 | 8/2010 | Ton et al. |
| 7,854,760 B2 | 12/2010 | Molaei et al. |
| 7,901,447 B2 | 3/2011 | Molaei et al. |
| 7,942,925 B2 | 5/2011 | Yodfat et al. |
| 8,007,529 B2 | 8/2011 | Yan |
| 8,092,486 B2 | 1/2012 | Berrada et al. |
| 8,092,508 B2 | 1/2012 | Leynov et al. |
| 8,192,484 B2 | 6/2012 | Frid |
| 8,382,825 B2 | 2/2013 | Garcia et al. |
| 8,394,119 B2 | 3/2013 | Zaver et al. |
| 8,398,701 B2 | 3/2013 | Berez et al. |
| 8,617,234 B2 | 12/2013 | Garcia et al. |
| 8,623,067 B2 | 1/2014 | Berez et al. |
| 8,628,564 B2 | 1/2014 | Berez et al. |
| 8,764,817 B2 | 7/2014 | Sheldon |
| 8,801,772 B2 | 8/2014 | Shobayashi et al. |
| 8,979,918 B2 | 3/2015 | Murayama |
| 9,050,205 B2 | 6/2015 | Berez et al. |
| 9,114,001 B2 | 8/2015 | Kusleika et al. |
| 9,125,659 B2 | 9/2015 | Berez et al. |
| 2001/0027338 A1 | 10/2001 | Greenberg |
| 2001/0044651 A1 | 11/2001 | Steinke et al. |
| 2001/0049547 A1 | 12/2001 | Moore |
| 2001/0056299 A1 | 12/2001 | Thompson |
| 2002/0004667 A1 | 1/2002 | Adams et al. |
| 2002/0007194 A1 | 1/2002 | Plowiecki |
| 2002/0029061 A1 | 3/2002 | Amplatz et al. |
| 2002/0035396 A1 | 3/2002 | Heath |
| 2002/0062091 A1 | 5/2002 | Jacobsen et al. |
| 2002/0078808 A1 | 6/2002 | Jacobsen et al. |
| 2002/0082558 A1 | 6/2002 | Samson et al. |
| 2002/0087119 A1 | 7/2002 | Parodi |
| 2002/0111633 A1 | 8/2002 | Stoltze et al. |
| 2002/0111648 A1 | 8/2002 | Kusleika et al. |
| 2002/0120323 A1 | 8/2002 | Thompson et al. |
| 2002/0138133 A1 | 9/2002 | Lenz et al. |
| 2002/0143361 A1 | 10/2002 | Douk et al. |
| 2002/0143384 A1 | 10/2002 | Ozasa |
| 2002/0169473 A1 | 11/2002 | Sepetka et al. |
| 2002/0169474 A1 | 11/2002 | Kusleika et al. |
| 2002/0173839 A1 | 11/2002 | Leopold et al. |
| 2002/0188314 A1 | 12/2002 | Anderson et al. |
| 2002/0193864 A1 | 12/2002 | Khosravi et al. |
| 2003/0009215 A1 | 1/2003 | Mayer |
| 2003/0023299 A1 | 1/2003 | Amplatz et al. |
| 2003/0069522 A1 | 4/2003 | Jacobsen et al. |
| 2003/0100945 A1 | 5/2003 | Yodfat et al. |
| 2003/0130684 A1 | 7/2003 | Brady et al. |
| 2003/0135258 A1 | 7/2003 | Andreas et al. |
| 2003/0163155 A1 | 8/2003 | Haverkost et al. |
| 2003/0163156 A1 | 8/2003 | Hebert et al. |

(56) References Cited

U.S. PATENT DOCUMENTS

| | | |
|---|---|---|
| 2003/0176884 A1 | 9/2003 | Berrada et al. |
| 2003/0187495 A1 | 10/2003 | Cully et al. |
| 2003/0212429 A1 | 11/2003 | Keegan et al. |
| 2003/0212430 A1 | 11/2003 | Bose et al. |
| 2004/0024416 A1 | 2/2004 | Yodfat et al. |
| 2004/0030265 A1 | 2/2004 | Murayama et al. |
| 2004/0044395 A1 | 3/2004 | Nelson |
| 2004/0073300 A1 | 4/2004 | Chouinard et al. |
| 2004/0088037 A1 | 5/2004 | Nachreiner et al. |
| 2004/0093010 A1 | 5/2004 | Gesswein et al. |
| 2004/0098099 A1 | 5/2004 | McCullagh et al. |
| 2004/0133223 A1 | 7/2004 | Weber |
| 2004/0153117 A1 | 8/2004 | Clubb et al. |
| 2004/0162606 A1 | 8/2004 | Thompson |
| 2004/0172055 A1 | 9/2004 | Huter et al. |
| 2004/0186368 A1 | 9/2004 | Ramzipoor et al. |
| 2004/0193178 A1 | 9/2004 | Nikolchev |
| 2004/0193179 A1 | 9/2004 | Nikolchev |
| 2004/0193208 A1 | 9/2004 | Talpade et al. |
| 2004/0199243 A1 | 10/2004 | Yodfat |
| 2004/0210235 A1 | 10/2004 | Deshmukh et al. |
| 2004/0215332 A1 | 10/2004 | Frid |
| 2004/0220585 A1 | 11/2004 | Nikolchev |
| 2004/0220608 A1 | 11/2004 | D'Aquanni et al. |
| 2004/0220663 A1 | 11/2004 | Rivelli |
| 2004/0254628 A1 | 12/2004 | Nazzaro et al. |
| 2004/0260331 A1 | 12/2004 | D'Aquanni et al. |
| 2005/0004595 A1 | 1/2005 | Boyle et al. |
| 2005/0021075 A1 | 1/2005 | Bonnette et al. |
| 2005/0033407 A1 | 2/2005 | Weber et al. |
| 2005/0038447 A1 | 2/2005 | Huffmaster |
| 2005/0051243 A1 | 3/2005 | Forbes Jones et al. |
| 2005/0055047 A1 | 3/2005 | Greenhalgh |
| 2005/0059889 A1 | 3/2005 | Mayer |
| 2005/0060017 A1 | 3/2005 | Fischell et al. |
| 2005/0090888 A1 | 4/2005 | Hines et al. |
| 2005/0101989 A1 | 5/2005 | Cully et al. |
| 2005/0137680 A1 | 6/2005 | Ortiz et al. |
| 2005/0149111 A1 | 7/2005 | Kanazawa et al. |
| 2005/0165441 A1 | 7/2005 | McGuckin et al. |
| 2005/0177186 A1 | 8/2005 | Cully et al. |
| 2005/0192620 A1 | 9/2005 | Cully et al. |
| 2005/0197689 A1 | 9/2005 | Molaei |
| 2005/0209672 A1 | 9/2005 | George et al. |
| 2005/0209678 A1 | 9/2005 | Henkes et al. |
| 2005/0246010 A1 | 11/2005 | Alexander et al. |
| 2005/0267568 A1 | 12/2005 | Berez et al. |
| 2005/0283220 A1 | 12/2005 | Gobran et al. |
| 2005/0288764 A1 | 12/2005 | Snow |
| 2005/0288766 A1 | 12/2005 | Plain et al. |
| 2006/0020324 A1 | 1/2006 | Schmid et al. |
| 2006/0036309 A1 | 2/2006 | Hebert et al. |
| 2006/0089703 A1 | 4/2006 | Escamilla et al. |
| 2006/0095213 A1 | 5/2006 | Escamilla et al. |
| 2006/0111771 A1 | 5/2006 | Ton et al. |
| 2006/0116713 A1 | 6/2006 | Sepetka et al. |
| 2006/0116750 A1 | 6/2006 | Hebert et al. |
| 2006/0184238 A1 | 8/2006 | Kaufmann et al. |
| 2006/0195118 A1 | 8/2006 | Richardson |
| 2006/0206148 A1 | 9/2006 | Khairkhahan et al. |
| 2006/0206200 A1 | 9/2006 | Garcia et al. |
| 2006/0206201 A1 | 9/2006 | Garcia et al. |
| 2006/0212127 A1 | 9/2006 | Karabey et al. |
| 2006/0271149 A1 | 11/2006 | Berez et al. |
| 2006/0271153 A1 | 11/2006 | Garcia et al. |
| 2006/0276910 A1 | 12/2006 | Weber |
| 2007/0021816 A1 | 1/2007 | Rudin |
| 2007/0043419 A1 | 2/2007 | Nikolchev et al. |
| 2007/0055365 A1 | 3/2007 | Greenberg et al. |
| 2007/0060994 A1 | 3/2007 | Gobran et al. |
| 2007/0073379 A1 | 3/2007 | Chang |
| 2007/0077347 A1 | 4/2007 | Richter |
| 2007/0100321 A1 | 5/2007 | Rudakov et al. |
| 2007/0100414 A1 | 5/2007 | Licata |
| 2007/0100430 A1 | 5/2007 | Rudakov et al. |
| 2007/0112415 A1 | 5/2007 | Bartlett |
| 2007/0119295 A1 | 5/2007 | McCullagh |
| 2007/0123969 A1 | 5/2007 | Gianotti |
| 2007/0162104 A1 | 7/2007 | Frid |
| 2007/0167980 A1 | 7/2007 | Figulla et al. |
| 2007/0198076 A1 | 8/2007 | Hebert et al. |
| 2007/0203559 A1 | 8/2007 | Freudenthal et al. |
| 2007/0203563 A1 | 8/2007 | Hebert et al. |
| 2007/0208367 A1 | 9/2007 | Fiorella et al. |
| 2007/0208373 A1 | 9/2007 | Zaver et al. |
| 2007/0208376 A1 | 9/2007 | Meng |
| 2007/0208415 A1 | 9/2007 | Grotheim et al. |
| 2007/0219619 A1 | 9/2007 | Dieck et al. |
| 2007/0225760 A1 | 9/2007 | Moszner et al. |
| 2007/0233175 A1 | 10/2007 | Zaver et al. |
| 2007/0239261 A1 | 10/2007 | Bose et al. |
| 2007/0255386 A1 | 11/2007 | Tenne |
| 2007/0255388 A1 | 11/2007 | Rudakov et al. |
| 2007/0280850 A1 | 12/2007 | Carlson |
| 2007/0299500 A1 | 12/2007 | Hebert et al. |
| 2007/0299501 A1 | 12/2007 | Hebert et al. |
| 2007/0299502 A1 | 12/2007 | Hebert et al. |
| 2008/0015673 A1 | 1/2008 | Chuter |
| 2008/0033341 A1 | 2/2008 | Grad |
| 2008/0033526 A1 | 2/2008 | Atladottir et al. |
| 2008/0039930 A1 | 2/2008 | Jones et al. |
| 2008/0039933 A1 | 2/2008 | Yodfat |
| 2008/0071351 A1 | 3/2008 | Flanagan et al. |
| 2008/0082154 A1 | 4/2008 | Tseng et al. |
| 2008/0114391 A1 | 5/2008 | Dieck et al. |
| 2008/0119943 A1 | 5/2008 | Armstrong et al. |
| 2008/0125855 A1 | 5/2008 | Henkes et al. |
| 2008/0208320 A1 | 8/2008 | Tan-Malecki et al. |
| 2008/0221666 A1 | 9/2008 | Licata et al. |
| 2008/0221670 A1 | 9/2008 | Clerc et al. |
| 2008/0221671 A1 | 9/2008 | Chouinard et al. |
| 2008/0255654 A1 | 10/2008 | Hebert et al. |
| 2008/0255655 A1 | 10/2008 | Kusleika et al. |
| 2008/0262590 A1 | 10/2008 | Murray |
| 2008/0269774 A1 | 10/2008 | Garcia et al. |
| 2008/0275497 A1 | 11/2008 | Palmer et al. |
| 2008/0275498 A1 | 11/2008 | Palmer et al. |
| 2008/0294104 A1 | 11/2008 | Mawad |
| 2008/0300667 A1 | 12/2008 | Hebert et al. |
| 2008/0300668 A1 | 12/2008 | Bonsignore |
| 2008/0300673 A1 | 12/2008 | Clerc et al. |
| 2009/0024202 A1 | 1/2009 | Dave et al. |
| 2009/0024205 A1 | 1/2009 | Hebert et al. |
| 2009/0030496 A1 | 1/2009 | Kaufmann et al. |
| 2009/0030497 A1 | 1/2009 | Metcalf et al. |
| 2009/0054981 A1 | 2/2009 | Frid et al. |
| 2009/0099643 A1 | 4/2009 | Hyodoh et al. |
| 2009/0105802 A1 | 4/2009 | Henry et al. |
| 2009/0105803 A1 | 4/2009 | Shelso |
| 2009/0125093 A1 | 5/2009 | Hansen |
| 2009/0192536 A1 | 7/2009 | Berez et al. |
| 2009/0192587 A1 | 7/2009 | Frid |
| 2009/0198318 A1 | 8/2009 | Berez et al. |
| 2009/0216307 A1 | 8/2009 | Kaufmann et al. |
| 2009/0222035 A1 | 9/2009 | Schneiderman |
| 2009/0270974 A1 | 10/2009 | Berez et al. |
| 2009/0287241 A1 | 11/2009 | Berez et al. |
| 2009/0287288 A1 | 11/2009 | Berez et al. |
| 2009/0288000 A1 | 11/2009 | McPherson |
| 2009/0292348 A1 | 11/2009 | Berez et al. |
| 2009/0318947 A1 | 12/2009 | Garcia et al. |
| 2009/0319017 A1 | 12/2009 | Berez et al. |
| 2010/0010624 A1 | 1/2010 | Berez et al. |
| 2010/0042200 A1 | 2/2010 | Richter et al. |
| 2010/0061604 A1 | 3/2010 | Nahm et al. |
| 2010/0063531 A1 | 3/2010 | Rudakov et al. |
| 2010/0070024 A1 | 3/2010 | Venturelli et al. |
| 2010/0076317 A1 | 3/2010 | Babic et al. |
| 2010/0152834 A1 | 6/2010 | Hannes et al. |
| 2010/0161025 A1 | 6/2010 | Kuppurathanam et al. |
| 2010/0174269 A1 | 7/2010 | Tompkins et al. |
| 2010/0174309 A1 | 7/2010 | Fulkerson et al. |
| 2010/0179583 A1 | 7/2010 | Carpenter et al. |
| 2010/0179647 A1 | 7/2010 | Carpenter et al. |

(56) References Cited

U.S. PATENT DOCUMENTS

| | | |
|---|---|---|
| 2010/0198334 A1 | 8/2010 | Yodfat et al. |
| 2010/0204779 A1 | 8/2010 | Schuessler et al. |
| 2010/0211154 A1 | 8/2010 | Murayama |
| 2010/0222864 A1 | 9/2010 | Rivelli, Jr. et al. |
| 2010/0241214 A1 | 9/2010 | Holzer et al. |
| 2010/0256732 A1 | 10/2010 | Shin et al. |
| 2010/0256733 A1 | 10/2010 | Schuessler |
| 2010/0280587 A1 | 11/2010 | Ortiz et al. |
| 2010/0318174 A1 | 12/2010 | Shaolian et al. |
| 2010/0318178 A1 | 12/2010 | Rapaport et al. |
| 2011/0016427 A1 | 1/2011 | Douen |
| 2011/0040372 A1 | 2/2011 | Hansen et al. |
| 2011/0046718 A1 | 2/2011 | Cattaneo |
| 2011/0046720 A1 | 2/2011 | Shalev et al. |
| 2011/0054589 A1 | 3/2011 | Bashiri et al. |
| 2011/0166592 A1 | 7/2011 | Garcia et al. |
| 2011/0166637 A1 | 7/2011 | Irwin et al. |
| 2011/0166639 A1 | 7/2011 | Pulnev et al. |
| 2011/0179389 A1 | 7/2011 | Douen |
| 2011/0184451 A1 | 7/2011 | Sahl |
| 2011/0190862 A1 | 8/2011 | Bashiri et al. |
| 2011/0245862 A1 | 10/2011 | Dieck et al. |
| 2011/0270178 A1 | 11/2011 | Fiorella et al. |
| 2012/0035643 A1 | 2/2012 | Khairkhahan et al. |
| 2012/0041459 A1 | 2/2012 | Fiorella et al. |
| 2012/0158124 A1 | 6/2012 | Zaver et al. |
| 2012/0253454 A1 | 10/2012 | Costello |
| 2012/0290067 A1 | 11/2012 | Cam |
| 2012/0316638 A1 | 12/2012 | Grad et al. |
| 2012/0323309 A1 | 12/2012 | Cattaneo |
| 2013/0116773 A1 | 5/2013 | Roeder et al. |
| 2013/0123901 A1 | 5/2013 | Connor et al. |
| 2013/0138202 A1 | 5/2013 | Paul et al. |
| 2013/0172975 A1 | 7/2013 | Berez et al. |
| 2013/0190856 A1 | 7/2013 | von Oepen et al. |
| 2013/0204347 A1 | 8/2013 | Armstrong et al. |
| 2013/0211489 A1 | 8/2013 | Makower et al. |
| 2013/0211497 A1 | 8/2013 | Charlebois et al. |
| 2013/0274849 A1 | 10/2013 | Zaver et al. |
| 2014/0018843 A1 | 1/2014 | Berez et al. |
| 2014/0074149 A1 | 3/2014 | Garcia et al. |
| 2014/0121744 A1 | 5/2014 | Kusleika |
| 2014/0121746 A1 | 5/2014 | Kusleika et al. |
| 2014/0128957 A1 | 5/2014 | Losordo et al. |
| 2014/0222130 A1 | 8/2014 | Kusleika |
| 2014/0316454 A1 | 10/2014 | Zaver et al. |
| 2014/0336741 A1 | 11/2014 | Connor et al. |
| 2015/0305748 A1 | 10/2015 | Berez et al. |
| 2015/0313736 A1 | 11/2015 | Berez et al. |
| 2015/0359646 A1 | 12/2015 | Kusleika et al. |

FOREIGN PATENT DOCUMENTS

| | | |
|---|---|---|
| EP | 1683541 A2 | 7/2006 |
| EP | 1942972 A1 | 7/2008 |
| EP | 1872742 B1 | 5/2009 |
| EP | 2 078 512 A1 | 7/2009 |
| FR | 2556210 B1 | 4/1988 |
| JP | 10-328216 A | 12/1998 |
| JP | 11-506686 | 6/1999 |
| JP | 11-299901 A | 11/1999 |
| JP | 2001-509412 A | 7/2001 |
| JP | 2002-253682 A | 9/2002 |
| JP | 2003-520103 A | 7/2003 |
| JP | 2004-049585 A | 2/2004 |
| JP | 2005-074230 A | 3/2005 |
| JP | 2006-506201 A | 2/2006 |
| JP | 2008-502378 A | 1/2008 |
| JP | 2008-541832 A | 11/2008 |
| WO | WO-88/00813 A1 | 2/1988 |
| WO | WO-95/09586 A1 | 4/1995 |
| WO | WO-95/32757 A1 | 12/1995 |
| WO | WO-98/04211 A1 | 2/1998 |
| WO | WO-98/47447 A1 | 10/1998 |
| WO | WO-99/02092 A1 | 1/1999 |
| WO | WO-99/05977 A1 | 2/1999 |
| WO | WO-99/49812 A3 | 12/1999 |
| WO | WO-01/05331 A1 | 1/2001 |
| WO | WO-01/52771 A1 | 7/2001 |
| WO | WO-02/05729 | 1/2002 |
| WO | WO-02/47579 | 6/2002 |
| WO | WO-02/054988 A3 | 1/2003 |
| WO | WO-03/007840 A2 | 1/2003 |
| WO | WO-03/043527 A2 | 5/2003 |
| WO | WO-03/049600 A2 | 6/2003 |
| WO | WO-03/057079 A1 | 7/2003 |
| WO | WO-03/073963 A2 | 9/2003 |
| WO | WO-2004/087006 A3 | 11/2004 |
| WO | WO-2005/021061 A2 | 3/2005 |
| WO | WO-2005/023149 A3 | 12/2005 |
| WO | WO-2006/034140 A2 | 3/2006 |
| WO | WO-2006/073745 A2 | 7/2006 |
| WO | WO-2006/127005 A1 | 11/2006 |
| WO | WO-2007/122396 A1 | 11/2007 |
| WO | WO-2008/005898 A2 | 1/2008 |
| WO | WO-2007/139689 A3 | 9/2008 |
| WO | WO-2007/139699 A3 | 9/2008 |
| WO | WO-2008/156683 A1 | 12/2008 |
| WO | WO-2005/115118 A3 | 7/2009 |
| WO | WO-2009/105710 A1 | 8/2009 |
| WO | WO-2010/127838 A2 | 11/2010 |
| WO | WO-2011/023105 A1 | 3/2011 |
| WO | WO-2011/134663 A2 | 11/2011 |

OTHER PUBLICATIONS

Brilstra, et al., Treatment of Intracranial Aneurysms by Embolization with Coils: A Systematic Review, Stroke, Journal of the American Heart Association, 1999, vol. 30, pp. 470-476.

Ferguson, Gary, Physical Factors in the Initiation, Growth and Rupture of Human Intracranial Saccular Aneurysms, J. Neurosurg, Dec. 1972, vol. 37, pp. 666-667.

Geremia, et al., Embolization of Experimentally Created Aneurysms with Intravascular Stent Devices, ANJR American Journal of Neuroradiology, Aug. 1994, vol. 15, pp. 1223-1231.

Geremia, et al., Occlusion of Experimentally Created Fusiform Aneurysms with Porous Metallic Stents, ANJR Am J Neuroradiol, Apr. 2000, Issue 21, pp. 739-745.

Lanzino, et al., Efficacy and Current Limitations of Intravascular Stents for Intracranial Internal Carotid, Vertebral, and Basilar Artery Aneurysms, Journal of Neurosurgery, Oct. 1999, vol. 91, Issue 4, pp. 538-546.

Lieber, et al., Alteration of Hemodynamics in Aneurysm Models by Stenting: Influence of Stent Porosity, Ann of Biomedical Eng., 1997, vol. 25, pp. 460-469, Buffalo, NY.

Lieber, et al., The Physics of Endoluminal Stenting in the Treatment of Cerebrovascular Aneurysms, Neurological Research, 2002, Vcol 24, Issue Supplement 1, pp. S32-S42.

Moss, et al., Vascular Occlusion with a Balloon-Expandable Stent Occluder, Radiology, May 1994, vol. 191, Issue 2, pp. 483-486.

Pereira, Edgard, History of Endovascular Aneurysm Occlusion, Management of Cerebral Aneurysms, 2004, pp. 11-26.

Qureshi, Adnan, Endovascular Treatment of Cerebrovascular Diseases and Intracranial Neoplasms, The Lancelet, Mar. 2004, vol. 363, pp. 804-813.

Steiger, Pathophysiology of Development and Rupture of Cerebral Aneurysms, Acta Nurochirurgica, Mar 1990, vol. Supplementum 48, Pages in 62 pages.

Tenaglia, et al., Ultrasound Guide Wire-Directed Stent Deployment, Duke University Medical Center, Department of Medicine, 1993 USA.

Yu, et al., A Steady Flow Analysis on the Stented and Non-Stented Sidewall Aneurysm Models, Medical Engineering and Physics, Apr. 1999, Issue 21, pp. 133-141.

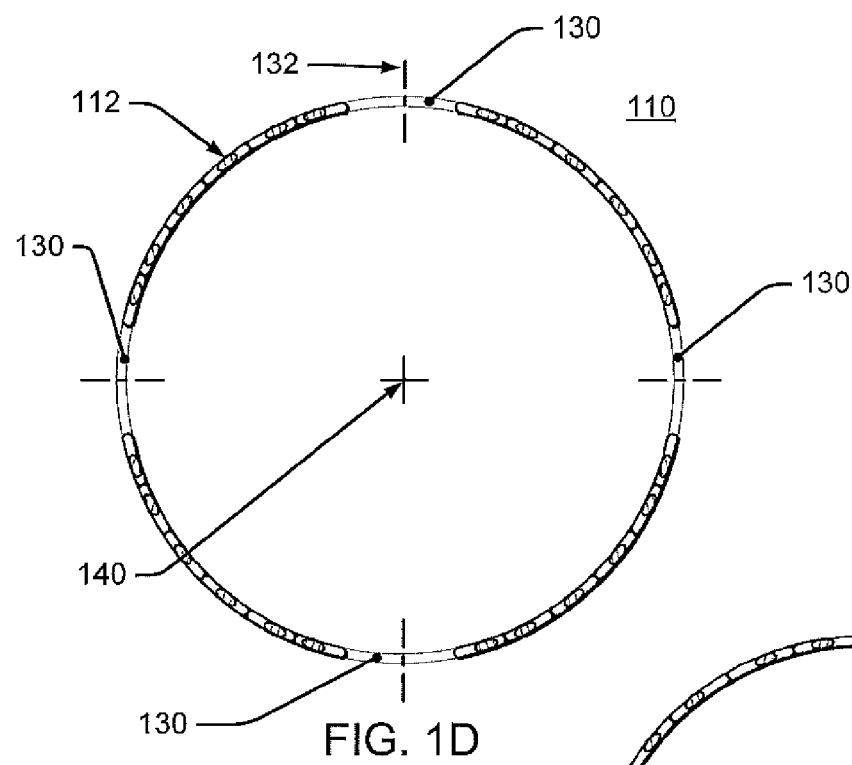
FIG. 1D
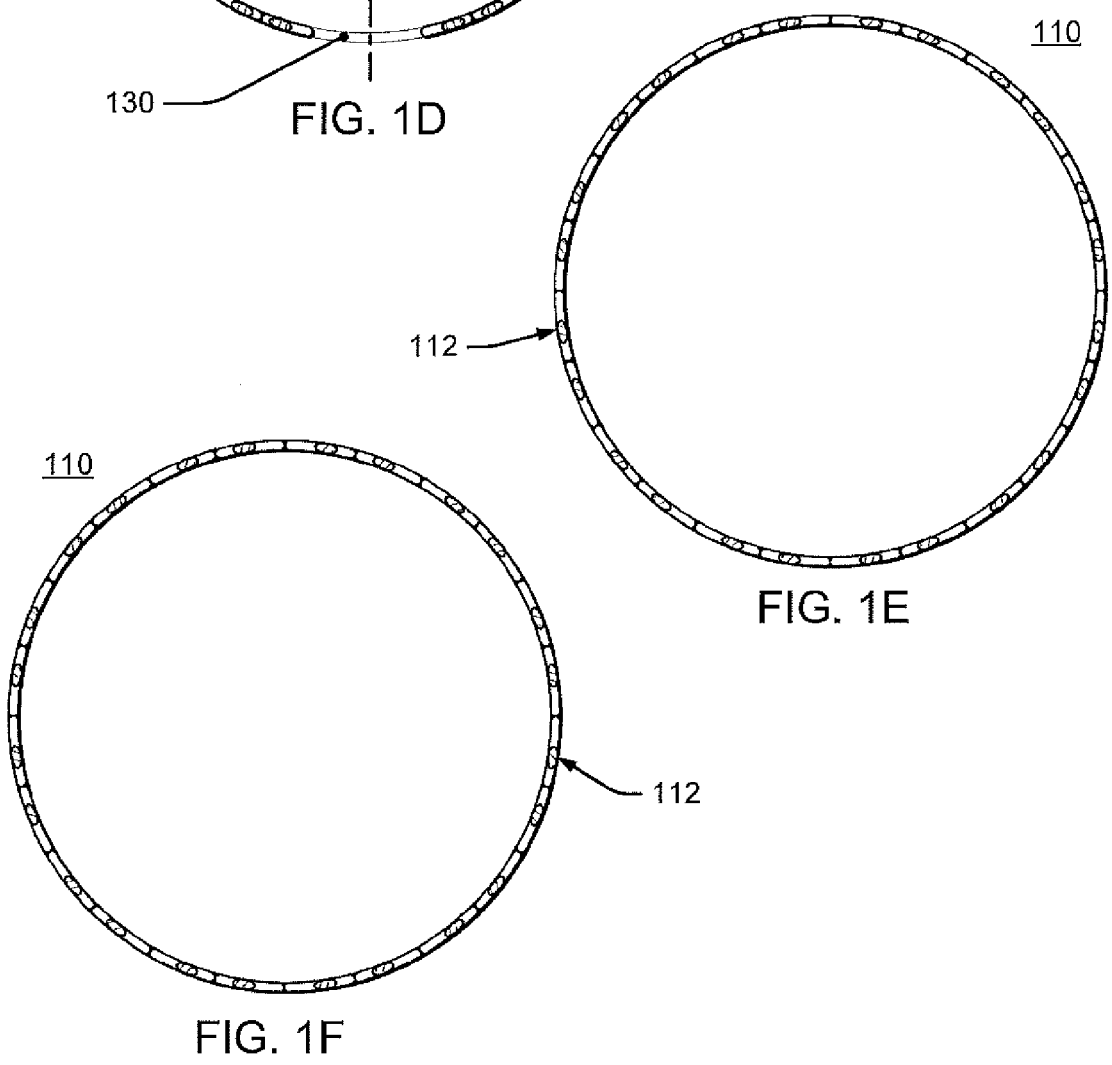
FIG. 1E
FIG. 1F

VASCULAR DEVICE FOR ANEURYSM TREATMENT AND PROVIDING BLOOD FLOW INTO A PERFORATOR VESSEL

RELATED APPLICATIONS

This application is a continuation of U.S. patent application Ser. No. 13/826,147, filed Mar. 14, 2013, now U.S. Pat. No. 9,157,174, which claims priority benefit of U.S. Provisional Application Ser. No. 61/760,907, filed Feb. 5, 2013, the entirety of each of which is hereby incorporated herein by reference.

BACKGROUND

Lumens in a patient's body can change in size, shape, and/or patency, and such changes can present complications or affect associated bodily functions. For example, the walls of the vasculature, particularly arterial walls, may develop a pathological dilatation, commonly called an aneurysm. Aneurysms are observed as a ballooning-out of the wall of an artery. This is a result of the vessel wall being weakened by disease, injury, or a congenital abnormality. Aneurysms have thin, weak walls and have a tendency to rupture and are often caused or made worse by high blood pressure. Aneurysms can be found in different parts of the body; the most common being abdominal aortic aneurysms (AAA) and the brain or cerebral aneurysms. The mere presence of an aneurysm is not always life-threatening, but an aneurysm can have serious health consequences such as a stroke if one should rupture in the brain. Additionally, a ruptured aneurysm can also result in death.

SUMMARY

The subject technology is illustrated, for example, according to various aspects described below. Various examples of aspects of the subject technology are described as numbered clauses (1, 2, 3, etc.) for convenience. These are provided as examples, and do not limit the subject technology. It is noted that any of the dependent clauses may be combined in any combination, and placed into a respective independent clause, e.g., clause 1, 18 and 27. The other clauses can be presented in a similar manner.

1. A vascular device, comprising:
   a body having a first, collapsed configuration and a second, expanded configuration, the body comprised of a plurality of heat-set strands;
   wherein the strands are braided such that when the body is in the second configuration, the strands form a plurality of pores and a plurality of apertures between the strands;
   wherein the apertures are disposed at a longitudinal center region of the body;
   wherein, when the body is in the second configuration, the pores at proximal and distal portions of the body are generally uniform in size and smaller in size than the apertures; and
   wherein the pores and the apertures are substantially the same size when the body is in the first configuration.
2. The vascular device of clause 1, wherein the apertures are formed by displacement of adjacent strands.
3. The vascular device of clause 1, wherein the plurality of apertures comprises two apertures.
4. The vascular device of clause 2, wherein the apertures are equally spaced and radially arranged around a longitudinal axis of the body.
5. The vascular device of clause 2, wherein a center region of each of the apertures is disposed along a single radial cross section of the body.
6. The vascular device of clause 1, wherein the plurality of apertures comprises three apertures.
7. The vascular device of clause 6, wherein the apertures are equally spaced and radially arranged around a longitudinal axis of the body.
8. The vascular device of clause 6, wherein a center region of each of the apertures is disposed along a single radial cross section of the body.
9. The vascular device of clause 1, wherein the plurality of apertures comprises four apertures.
10. The vascular device of clause 9, wherein the apertures are equally spaced and radially arranged around a longitudinal axis of the body.
11. The vascular device of clause 9, wherein a center region of each of the apertures is disposed along a single radial cross section of the body.
12. The vascular device of clause 1, wherein a number of strands in each of a proximal, center, and distal radial cross sections of the body is the same.
13. The vascular device of clause 1, wherein the body has a hoop strength that is generally uniform along the body's longitudinal length.
14. The vascular device of clause 1, wherein an area of at least one of the apertures is about 0.005 square millimeters or larger.
15. The vascular device of clause 1, wherein an area of at least one of the pores is about 0.01 square millimeters or smaller.
16. The vascular device of clause 1, wherein the apertures are larger than the pores.
17. The vascular device of clause 1, wherein a thickness of each strand is about 0.0010 to 0.0014 inches.
18. A method, for creating a plurality of apertures in a vascular device, comprising:
   braiding a plurality of shape-memory strands to form the vascular device, wherein the strands are braided to form a plurality of pores between the strands, wherein the pores at proximal and distal portions of the device are generally uniform in size;
   forming each of the apertures by displacing strands disposed at a longitudinal center region of the device with a tapered mandrel, wherein each aperture is larger than a pore; and
   applying heat to the displaced strands to thereby set a shape of the displaced strands.
19. The method of clause 18, wherein the plurality of apertures comprises two apertures.
20. The method of clause 18, wherein the plurality of apertures comprises three apertures.
21. The method of clause 18, wherein the plurality of apertures comprises four apertures.
22. The method of clause 18, wherein the apertures are equally spaced and radially arranged around a longitudinal axis of the vascular device.
23. The method of clause 18, wherein a center region of each of the apertures is disposed along a single radial cross section of the vascular device.
24. The method of clause 18, wherein a number of strands in each of a proximal, center, and distal radial cross sections of the vascular device is the same.
25. The method of clause 18, wherein the vascular device has a hoop strength that is generally uniform along the device's longitudinal length.

26. The method of clause 18, wherein the apertures are larger than the pores.

27. A method for providing blood flow into a perforator vessel extending from a sac of an aneurysm, the method comprising:

positioning a vascular device in a vessel at an opening into the aneurysm, wherein the device has a first, collapsed configuration and a second, expanded configuration, the device comprising:

a plurality of heat-set strands, wherein the strands are braided such that when the device is in the second configuration, the strands form a plurality of pores and a plurality of apertures between the strands;

wherein the apertures are disposed at a longitudinal center region of the device;

wherein, when the device is in the second configuration, the pores at proximal and distal portions of the device are generally uniform in size and smaller in size than the apertures; and wherein the pores and the apertures are substantially the same size when the device is in the first configuration; and aligning the longitudinal center region of the device with the aneurysm to thereby provide blood flow into the perforator through one of the apertures.

28. The method of clause 27, wherein the plurality of apertures comprises two apertures.

29. The method of clause 27, wherein the plurality of apertures comprises three apertures.

30. The method of clause 27, wherein the plurality of apertures comprises four apertures.

31. The method of clause 27, wherein the apertures are equally spaced and radially arranged around a longitudinal axis of the vascular device.

32. The method of clause 27, wherein a center region of each of the apertures is disposed along a single radial cross section of the vascular device.

33. The method of clause 27, wherein a number of strands in each of a proximal, center, and distal radial cross sections of the vascular device are the same.

34. The method of clause 27, wherein the vascular device has a hoop strength that is generally uniform along the device's longitudinal length.

35. The method of clause 27, wherein the apertures are larger than the pores.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

A detailed description will be made with reference to the accompanying drawings:

FIG. 1D depicts a cross section taken at a longitudinal center of a vascular device, according to some embodiments of the subject technology.

FIG. 1E depicts a cross section taken at a proximal region of a vascular device, according to some embodiments of the subject technology.

FIG. 1F depicts a cross section taken at a distal region of a vascular device, according to some embodiments of the subject technology.

DETAILED DESCRIPTION

Aneurysms may be located, for example, along vessel side walls. A neck of an aneurysm typically defines an opening of between about 2 to 25 mm, though other sizes and ranges are also possible. The neck connects an anatomical vessel lumen to a fundus of the aneurysm. In some instances, "vessel" may refer to blood vessels (including arteries and veins) or other suitable body organs having a lumen, such as the gastrointestinal tract (e.g., esophagus, stomach, small intestine, colon, rectum), bile ducts, urinary bladder, ureter, urethra, trachea, bronchi, and the like. Blood flow within the anatomical lumen is channeled through the neck and into the fundus. In response to the constant blood flow into the fundus of the aneurysm, the wall of the aneurysm continues to distend and presents a significant risk of rupturing. When the blood within the aneurysm causes pressure against the wall of the aneurysm that exceeds the wall strength, the aneurysm ruptures.

Reduction of blood flow to or within the aneurysm results in a reduction in force against the wall of the aneurysm and a corresponding reduction in the risk of rupturing. Conventionally, a reduction of the force and volume of blood entering the aneurysm may be accomplished by an occluding device. The conventional occluding device restricts blood flow to the aneurysm. The aneurysm, however, may have small perforator vessels or arteries extending from the aneurysm. Because the conventional occluding device isolates the aneurysm from the blood flow in the vessel, any small perforator arteries or vessel branches (both inlet and outlet branches) extending from the aneurysm are also occluded, thereby preventing blood from flowing into the perforator vessels.

The vascular devices of the subject technology solve some or all of the foregoing problems by sufficiently restricting the blood flow into the aneurysm to prevent rupture while providing sufficient blood flow to perforator vessels or arteries extending from the aneurysm, or extending from the parent vessel sidewall near the aneurysm neck (and/or from a location on the sidewall between the proximal and distal ends of the vascular device when deployed). The vascular device includes an expandable vascular device having one or more enlarged apertures disposed near the neck of the aneurysm. The vascular device is configured to reduce the laminar flow into the aneurysm to prevent rupture, while providing sufficient blood flow to the perforator vessel through one or more of the enlarged apertures. Accordingly, the vascular device exhibits a porosity configured to reduce haemodynamic flow into the aneurysm, but simultaneously allow perfusion to perforator vessels.

Figure 1A:
FIG. 1A depicts a vascular device in a collapsed configuration, according to some embodiments of the subject technology.
Figure 1B:
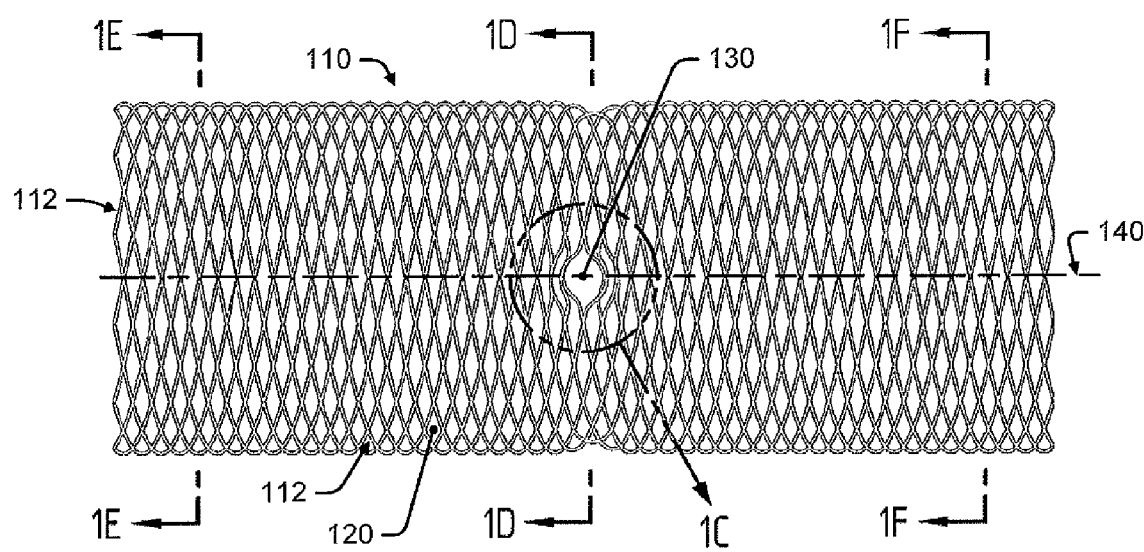
FIG. 1B depicts a vascular device in an expanded configuration, according to some embodiments of the subject technology.

FIGS. 1A-1F depict a vascular device 100, according to some embodiments of the subject technology. The vascular device 100 comprises a body 110 having a first, collapsed configuration and a second, expanded configuration. The body is comprised of a plurality of heat-set strands 112 that are braided such that when the body 110 is in the expanded configuration, the strands 112 form a plurality of pores 120 and a plurality of apertures 130 between the strands 112, as shown in FIG. 1B. When the body 110 is in the expanded configuration, the pores 120 at proximal and distal portions of the body 110 are generally uniform in size and smaller in size than the apertures 130. Referring to FIG. 1A, when the body 110 is in the collapsed configuration, the pores 120 and the apertures 130 are substantially the same size.

The body 110 may be a self-expanding stent made of two or more round or ovoid wire strands or filaments 112. In one aspect, the filaments may all be of the same thickness. For example, the thickness of each strand 112 may be about 0.0001 to 0.0020 inches. The filaments may be formed of known flexible and shape memory materials, such as nitinol. The filaments may be formed of platinum and stainless steel. The body 110 may be fabricated from platinum/8% tungsten and 35N LT (cobalt nickel alloy, which is a low titanium version of MP35N alloy) alloy wires. In other embodiments, one or more of the filaments can be formed of a biocompatible metal material or a biocompatible polymer, so long as the filaments are flexible and have shape memory properties. The filaments may be braided into a resulting lattice-like structure. In at least one embodiment, during braiding or winding of the body 110, the filaments may be loosely braided using a 1-over-2-under-2 system. In other embodiments, however, other methods of braiding may be followed, without departing from the scope of the disclosure.

The ends of the body 110 may be cut to length and therefore remain free for radial expansion and contraction. The body 110 may exhibit a high degree of flexibility due to the materials used, the porosity of the body 110, and the fact that the ends of the filaments are not secured to each other.

The pores 120 at the proximal and distal portions of the body 110 are sized to reduce haemodynamic flow into an aneurysm and the apertures 130 are sized to provide sufficient blood flow to any perforator vessels extending from the aneurysm. For example, an area of at least one of the pores 120 may be about 0.01 square millimeters or less and an area of at least one of the apertures 130 may be about 0.005 square millimeters or more. In some aspects, the apertures 130 are larger than the pores 120. In some embodiments, the apertures 130 are configured to be about five times the size of the pores 120. In some embodiments, the apertures 130 are sized to be range from about two to about ten times the size of the pores 120, while in some embodiments, the apertures 130 are sized to range from about three to about seven times the size of the pores 120.

Figure 1C:
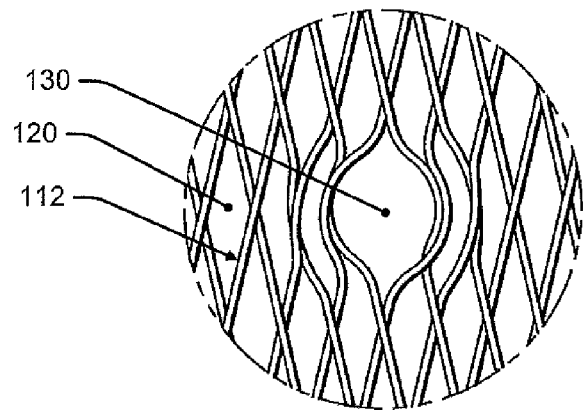
FIG. 1C depicts a detail view of an aperture, according to some embodiments of the subject technology.

The apertures 130 may be disposed at a longitudinal center region of the body 110 and be formed by displacement of adjacent strands, as shown in FIG. 1C. In one aspect, the vascular device 100 may have two apertures 130 disposed at the longitudinal center region of the body 110. In another example, the vascular device 100 may have three apertures 130 disposed at the longitudinal center region of the body 110. In yet another example, the vascular device 100 may have four apertures 130 disposed at the longitudinal center region of the body 110. Although FIGS. 1A-D depict four apertures 130, it is understood that a number of apertures greater than four may be suitable for many applications. The apertures 130 may be equally spaced and radially arranged around a longitudinal axis 140 of the body. In some aspects, a center region 132 of each of the apertures 130 is disposed along a single radial cross section of the body 110, as shown in FIG. 1D.

In some aspects, because the pores 120 and the apertures 130 generally comprise gaps, voids, or areas that are formed between adjacent strands 112, the number of strands 112 in each of a proximal, center, and distal radial cross sections of the body 110 is the same. For example, referring to FIGS. 1D-1F, the number of strands 112 shown at the proximal cross section of the body 110, shown in FIG. 1E, is the same as the number of strands 112 shown at the center cross section of the body 110, shown in FIG. 1D, and the distal cross section of the body 110, shown in FIG. 1F. Because the number of strands 112 at each of the proximal, center, and distal radial cross sections of the body 110 is the same, the body 110 has a hoop strength that is generally uniform along the body's 110 longitudinal length.

In one aspect, the apertures 130 may be formed on the vascular device 100 by first placing the vascular device 100 in the expanded configuration on a fixture and then inserting one or more tapered mandrels, depending on the number of apertures 130, through the body 110 to displace the strands 112 and thereby form the apertures 130. The displaced strands 112 are then heated to their shape memory temperature to "set" the displaced strands in their displaced configuration. Thereafter, the one or more mandrels are removed from the body 110 and the apertures 130 remain formed on the body 110.

When the vascular device 100 is in the collapsed configuration, the displaced strands 112 forming the apertures 130 are collapsed, along with all the strands 112 comprising the body 110, and the apertures 130 and the pores 120 are substantially the same size, as shown in FIG. 1A.

In one aspect, the vascular device may be coated with an endothelial progenitor cell coating to promote endothelium growth on an inner surface of the vascular device 100. Typically, the endothelium will grow from the proximal and/or distal ends of the vascular device 100 and traverse toward the longitudinal center of the vascular device 100. The strands 112 of the vascular device 100 serve as a substrate for the cells to attach thereto. As the inner surface of the vascular device becomes endothelialized, the pores 120 are occluded. Because the apertures 130 are larger than the pores 120, the endothelium grows around the apertures 130 but does not occlude the apertures 130. Accordingly, the apertures 130 remain unobstructed and permit blood to flow therethrough to feed any perforator vessel emanating from an aneurysm fundus, or emanating from the parent vessel sidewall near the aneurysm neck (and/or from a location on the sidewall between the proximal and distal ends of the vascular device when deployed).

Radiopaque markers may be located adjacent the proximal or distal portions of the vascular device 100, and may be located at any position along the length of the vascular device 100 between a proximal and distal end of the vascular device 100. The markers may be attached to the vascular device 100 by techniques such as adhesives, heat fusion, interference fit, fasteners, intermediate members, coatings, or by other techniques.

In some embodiments, the markers are comprised of ultrasonic markers, MRI-safe markers, or other markers. In some embodiments ultrasonic markers permit a physician to accurately determine the position of the vascular device 100 within a patient under ultrasonic visualization. Materials for an ultrasonic marker have an acoustical density sufficiently different from the vascular device 100 to provide suitable visualization via ultrasonic techniques. Exemplary materials comprise polymers, metals such as tantalum, platinum, gold, tungsten and alloys of such metals, hollow glass spheres or microspheres, and other materials.

In some embodiments, MRI-safe markers permit a physician to accurately determine the position of the vascular device 100 within a patient under magnetic resonance imaging. Exemplary materials for making MRI-safe marker have a magnetic signature sufficiently different from the vascular device 100 to provide suitable visualization via MRI techniques. Exemplary materials comprise polymers, metals such as tantalum, platinum, gold, tungsten and alloys of such metals, non-ferrous materials, and other materials.

A technique for treating an aneurysm and providing blood flow into a perforator vessel extending from a sac of the aneurysm will now be discussed with reference to FIGS. 2-5. The vascular device 100 may be delivered to a treatment site using a delivery system 200. The delivery system 200 may include a catheter, which may for example, be an over the wire (OTW) catheter, a rapid exchange (multiple lumen) catheter, or a fixed wire catheter.

Prior to delivery, an outer sheath 210 is disposed over the vascular device 100 to confine the vascular device 100 in the first, collapsed configuration. The vascular device 100 is cooperatively movable within the outer sheath 210 in order to deliver the vascular device 100 to a treatment site, such as an aneurysm 310, within the vasculature 300 of a patient.

The outer sheath 210 may be configured to be introduced and advanced through the vasculature of the patient. The outer sheath 210 may be made from various thermoplastics, e.g., PTFE, FEP, HDPE, PEEK, etc., which may optionally be lined on the inner surface of the outer sheath 140 or an adjacent surface with a hydrophilic material such as PVP or some other plastic coating. Additionally, either surface may be coated with various combinations of different materials, depending upon the desired results.

The delivery system 200 also includes a shaft 220 and a guide wire 230. The shaft 220 has a guide wire lumen for allowing the guide wire 230 to extend therethrough. The shaft 220 may also include a reduced diameter at a distal region to provide sufficient annular space in which the vascular device 100 may be stowed.

Radiopaque markers may be provided at various locations along the length of the delivery system 200. For example, an enlarged distal tip 240 of the shaft 220 may be radiopaque. In another example, radiopaque markers may be provided on the reduced diameter distal region of the shaft 220, beneath the distal and proximal end of the vascular device 100. In yet another example, a radiopaque marker 250 may be disposed on the shaft 220 adjacent to a longitudinal center of the vascular device 100, corresponding to the location of the apertures 130.

In one aspect, the vascular device 100 may be configured with differently sized apertures 130 and/or number of apertures 130. A physician may therefore select the appropriate vascular device 100 based on a size of the aneurysm and/or a number of perforators extending from the aneurysm and the diameter of each aperture 130 and/or number of apertures 130 per vascular device 100. For example, based on the diameter of each aperture 130 and the number of perforators extending from the aneurysm sac and/or from the parent vessel 300, the vascular device 100 may be selected such that the apertures 130 in fluid communication with the sac (and/or with other relevant vessel location(s)) are sufficiently large to provide sufficient blood flow to each of the perforators when the vascular device 100 is in the second, expanded configuration. The blood flow permitted by the apertures 130 to the perforators is sufficient to provide blood to downstream tissues without inducing ischemia.

In another example, based on the number of apertures 130 in the vascular device 100 and the number of perforators extending from the aneurysm sac and/or from the parent vessel 300, the vascular device 100 may be selected such that there are a sufficient number of apertures 130 in fluid communication with the sac (and/or with other relevant vessel location(s)) to provide sufficient blood flow to each of the perforators when the vascular device 100 is in the second, expanded configuration. In these applications, sufficient blood flow is provided for the perforators extending from the aneurysm sac and/or parent vessel 300 to avoid or limit ischemia to downstream tissue, but the blood flow within the aneurysm is disrupted sufficiently to permit healing of the aneurysm.

Figure 2:
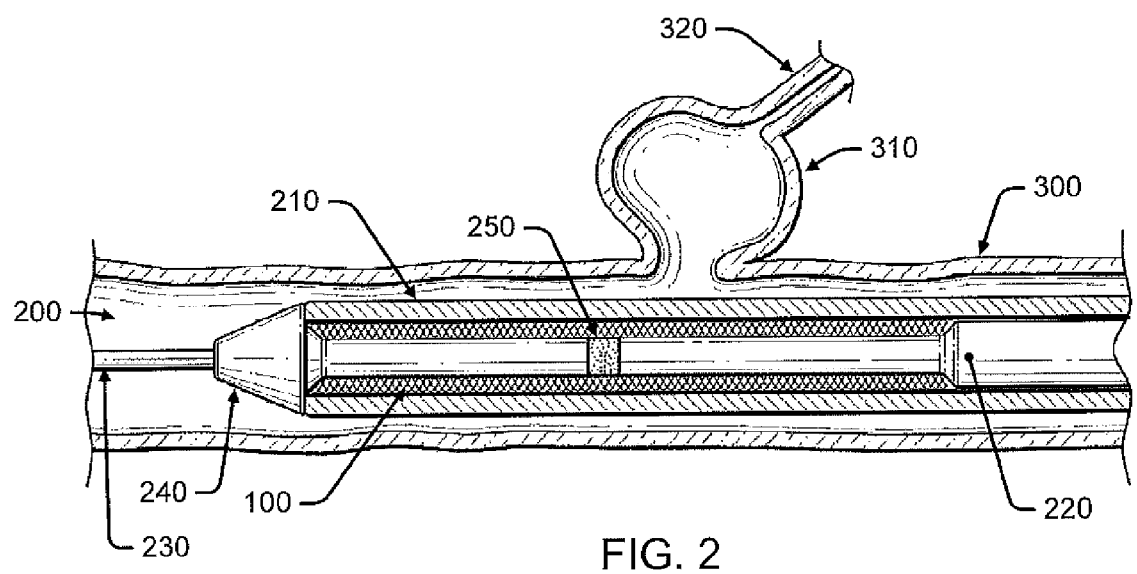
FIG. 2 depicts a cross section view of a vessel and delivery of a vascular device, according to some embodiments of the subject technology.

Referring to FIG. 2, the delivery system 200 is advanced percutaneously over the guide wire 230, in this example, to the site of the aneurysm 310 having a perforator vessel 320 extending therefrom.

Figure 3:
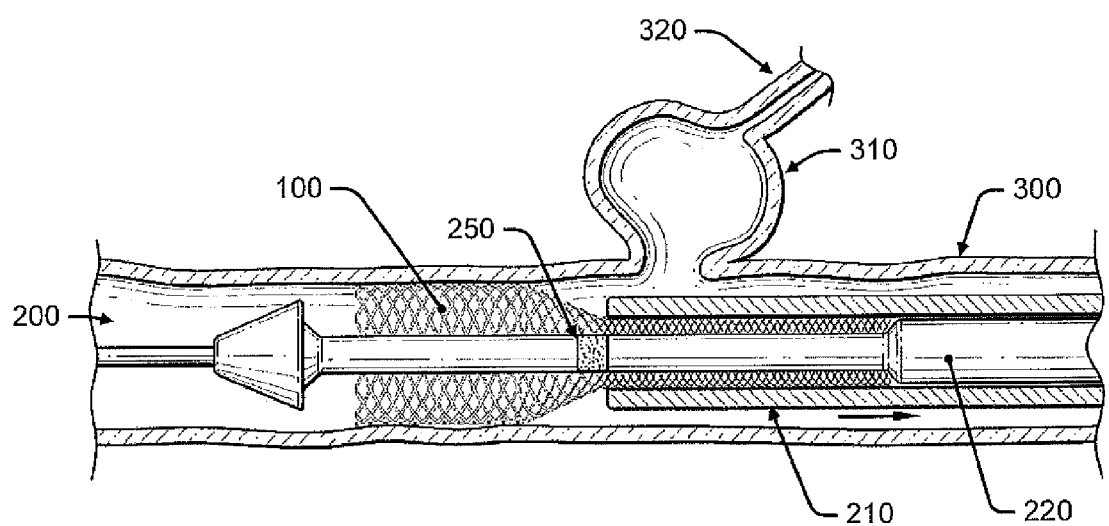
FIG. 3 depicts a cross section view of a vessel and delivery of a vascular device, according to some embodiments of the subject technology.

Referring to FIG. 3, after navigating the system 200 to the treatment site within the patient, the outer sheath 210 is withdrawn proximally while maintaining the position of the shaft 220 to thereby expose a distal portion of the shaft 220 and the vascular device 100. The outer sheath 210 is withdrawn until a distal end of the outer sheath 210 is proximal of the vascular device 100. As the outer sheath 210 is withdrawn, the vascular device 100 expands. During expansion, the apertures 130 may begin to take form due to the shape memory properties of the strands 112.

Figure 4:
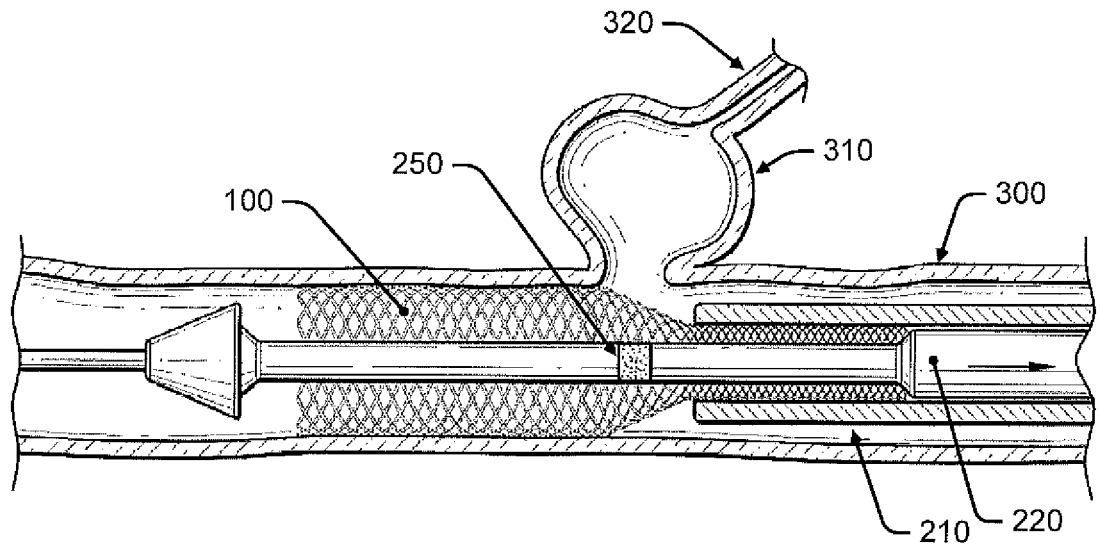
FIG. 4 depicts a cross section view of a vessel and delivery of a vascular device, according to some embodiments of the subject technology.
Figure 5:
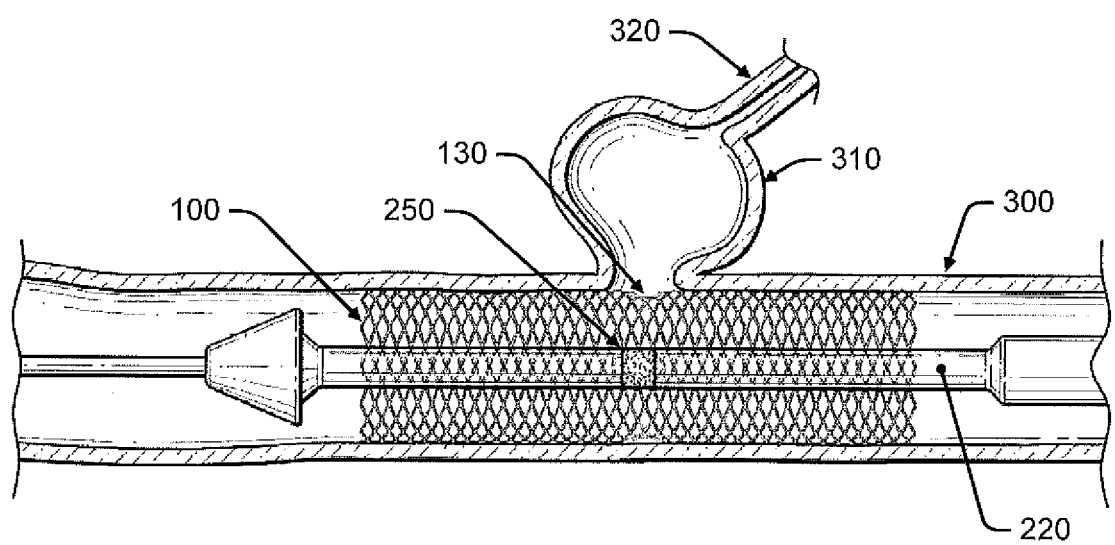
FIG. 5 depicts a cross section view of a vessel and delivery of a vascular device, according to some embodiments of the subject technology.

Referring to FIGS. 4 and 5, the delivery system 200 may be adjusted or withdrawn proximally during deployment, until the radiopaque marker 250 and hence the apertures 130 are centered along the length of the ostium or neck of the aneurysm 310 and/or located on either side of the ostium, as appropriate. In other words, the longitudinal center region of the vascular device 100, the region having the apertures 130, is aligned with the aneurysm 310 to thereby provide blood flow into the perforator 320 through one of the apertures 130. In one aspect, the longitudinal center region of the vascular device 100 is centered along the length of the ostium so that at least one aperture 130 provides blood flow to the perforator 320 when the vascular device 110 is in the second, expanded configuration.

In one aspect, during deployment, the position of the vascular device 100 within the vessel 300 may be further modified, if after initial partial deployment of the vascular device 100, the vascular device is positioned incorrectly or otherwise has to be relocated to properly cover the treatment site. For example, the outer sheath 210 may be advanced distally, thereby encapsulating or compressing the vascular device 100 within the outer sheath 210 and allowing the system 200 to be repositioned. Accordingly, the vascular device 100 may be partially deployed, resheathed, and relocated multiple times in order to ensure that the vascular device is properly deployed in the correct location.

In another aspect, because of the woven or braided structure of the vascular device 100, the strands of the vascular device 100 can also move relative to each other, further allowing the vascular device 100 to flex and thereby permit advancement or rotation of the unexpanded portion of the vascular device 100 against an expanded portion of the vascular device 100 that is deployed within the vessel 300. Accordingly, through rotation or positioning of the unexpanded portion relative to the expanded portion of the vascular device 100, the apertures 130 of the vascular device 100 may be properly aligned and positioned at the treatment site.

Figure 6:
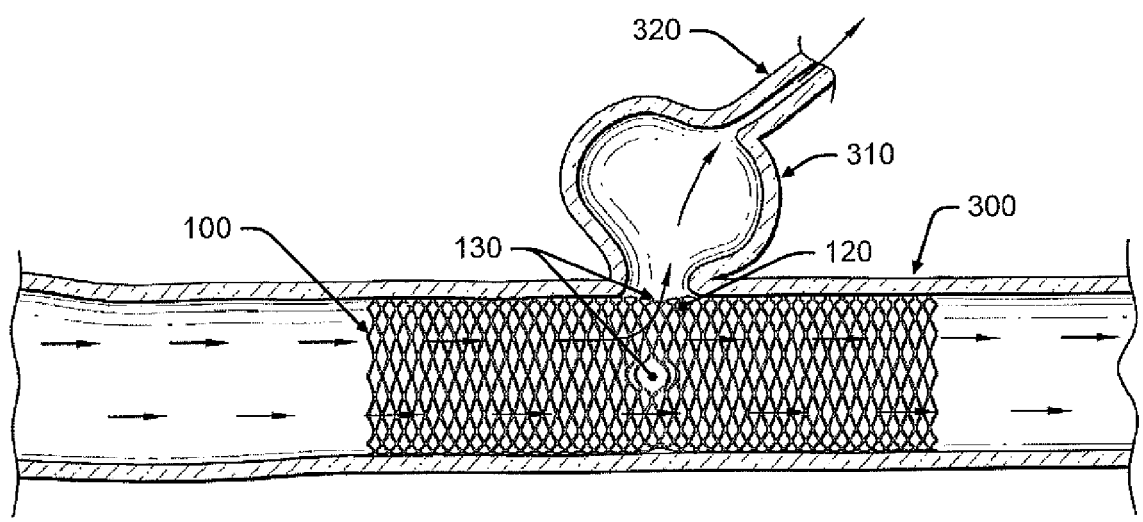
FIG. 6 depicts a cross section view of a vessel and deployed vascular device, according to some embodiments of the subject technology.

Referring to FIG. 6, once the entire vascular device 100 is fully expanded, the catheter, along with the outer sheath 210, shaft 220, and guide wire 230 may be withdrawn from the patient.

Initially, blood may flow to the perforator vessel 320 from the plurality of pores 120 and apertures 130. As the inner surface of the vascular device 100 becomes endothelialized, the pores 120 will become occluded thereby preventing blood from flowing therethrough. The blood, however, will continue to flow through the apertures 130, thereby providing sufficient blood flow to the perforator 320.

In one arrangement, the vascular device 100 may be comprised of metal, polymer, ceramic, permanent enduring materials, and may comprise either or both of non-bioabsorbable and bioabsorbable materials. Exemplary materials include, but are not limited to, NITINOL®, stainless steel, cobalt chromium alloys, Elgiloy, magnesium alloys, polylactic acid, poly glycolic acid, poly ester amide (PEA), poly ester urethane (PEU), amino acid based bioanalogous polymers, tungsten, tantalum, platinum, polymers, bio-polymers, ceramics, bio-ceramics, or metallic glasses. Part or all of the medical device may elute over time substances such as drugs, biologics, gene therapies, antithrombotics, coagulants, anti-inflammatory drugs, immunomodulator drugs, anti-proliferatives, migration inhibitors, extracellular matrix modulators, healing promoters, re-endothelialization promoters, or other materials. In some embodiments, the vascular device 100 may be formed from materials having shape memory properties. In some embodiments, the vascular device 100 may be finished by processes to remove slag. In some embodiments, the vascular device 100 may be subjected to a tempering treatment at temperatures customarily applied to the material so that the impressed structure is permanently established.

The vascular device 100 may have various lengths and diameters. For example, the vascular device 100 may have specific cross-sectional diameters, the diameters being measured when the vascular device 110 is fully free to expand, ranging from about 2 mm to about 6 mm. If the vascular device 110 has a diameter between about 3 mm and about 4 mm, it may be used in a size 18 microcatheters (i.e., microcatheters with an inner diameter of approximately 0.21 inch). If the vascular device 100 has a diameter between about 5 mm and about 6 mm, it may be used in a size 27 microcatheters (i.e., microcatheters with an inner diameter of approximately 0.027 inch). However, other suitable cross-sectional diameters may be used without deviating from the scope of the subject technology. In some embodiments, the vascular device 100 may have lengths, measured proximally to distally along the longitudinal axis of the vascular device 100, ranging from about 15 mm to about 40 mm, though other ranges and sizes are also possible.

The detailed description set forth above is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be apparent to those skilled in the art that the subject technology may be practiced without these specific details. In some instances, well-known structures and components are shown in block diagram form in order to avoid obscuring the concepts of the subject technology.

Skilled artisans may implement the described functionality in varying ways for each particular application. Various components and blocks may be arranged differently (for example, arranged in a different order, or partitioned in a different way) all without departing from the scope of the subject technology. It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

The previous description is provided to enable any person skilled in the art to practice the various aspects described herein. The previous description provides various examples of the subject technology, and the subject technology is not limited to these examples. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (for example, his) include the feminine and neuter gender (for example, her and its) and vice versa. Headings and subheadings, if any, are used for convenience only and do not limit the invention.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "aspect" does not imply that such aspect is essential to the subject technology or that such aspect applies to all configurations of the subject technology. A disclosure relating to an aspect may apply to all aspects, or one or more aspects. An aspect may provide one or more examples. A phrase such as an "aspect" may refer to one or more aspects and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such as a "configuration" may refer to one or more configurations and vice versa.

The word "exemplary" is used herein to mean "serving as an example or illustration." Any aspect or design described herein as "exemplary" is not necessarily to be construed as preferred or advantageous over other aspects or designs.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. §112, sixth paragraph, unless the element is expressly recited using the phrase "means for" or, in the case of a method claim, the element is recited using the phrase "step for." Furthermore, to the extent that the term "include," "have," or the like is used in the description or the claims, such term is intended to be inclusive in a manner similar to the term "comprise" as "comprise" is interpreted when employed as a transitional word in a claim.

What is claimed is:

1. A method, comprising:
    positioning, at a location within a blood vessel adjacent to an aneurysm, a vascular device having a body in a first, collapsed configuration with the body comprising braided strands forming pores and apertures between the strands, and the body having a longitudinally central section; and
    expanding the body from the first, collapsed configuration to a second, expanded configuration, wherein the pores are generally uniform in size and smaller in size than the apertures in the second, expanded configuration, the apertures being disposed at the longitudinally central section of the body and spaced apart from one another by the pores such that at least one of the apertures is adjacent to an ostium of the aneurysm, wherein blood flows into the aneurysm preferentially through the at least one aperture as compared to the pores.

2. The method of claim 1, wherein central regions of the apertures are disposed along a single radial cross section of the body.

3. The method of claim 2, wherein the body has a hoop strength that is generally uniform along a longitudinal length of the body.

4. The method of claim 1, wherein the body has a hoop strength that is generally uniform along a longitudinal length of the body.

5. The method of claim 1, wherein the pores and apertures are substantially the same size as each other in the first, collapsed configuration.

6. The method of claim 1, wherein the expanding comprises aligning at least one of the apertures to be adjacent to an opening of a perforator vessel.

7. The method of claim 1, wherein the apertures comprises four apertures.

8. The method of claim 1, wherein, in the second, expanded configuration, the apertures are equally spaced and radially arranged around a longitudinal axis of the body.

9. The method of claim 1,
    wherein, in the second, expanded configuration, an area of at least one of the apertures is 0.005 square millimeters or larger;
    wherein, in the second, expanded configuration, an area of at least one of the pores is 0.01 square millimeters or smaller; and
    wherein a thickness of each strand is 0.0010 to 0.0014 inches.

10. A method, comprising:
    positioning, at a target location within a blood vessel, a vascular device having a body in a first, collapsed configuration with the body comprising braided strands forming pores and apertures between the strands, the pores and the apertures being substantially the same size as each other in the first, collapsed configuration; and
    expanding the body from the first, collapsed configuration to a second, expanded configuration, wherein the pores have a first size and the apertures have a second size larger than the first size in the second, expanded configuration, the apertures being disposed at a longitudinally central section of the body, the pores being disposed at longitudinally proximal and distal sections of the body and between the apertures at the longitudinally central section of the body;
    wherein blood flows preferentially through the apertures as compared to the pores.

11. The method of claim 10, wherein the expanding comprises aligning at least one of the apertures to be adjacent to an ostium of an aneurysm.

12. The method of claim 10, wherein the expanding comprises aligning at least one of the apertures to be adjacent to an opening of a perforator vessel.

13. The method of claim 10, wherein the apertures comprises four apertures.

14. The method of claim 10, wherein, in the second, expanded configuration, the apertures are equally spaced and radially arranged around a longitudinal axis of the body.

15. The method of claim 10,
    wherein, in the second, expanded configuration, an area of at least one of the apertures is 0.005 square millimeters or larger;
    wherein, in the second, expanded configuration, an area of at least one of the pores is 0.01 square millimeters or smaller; and
    wherein a thickness of each strand is 0.0010 to 0.0014 inches.

16. A method, comprising:
    positioning, at a target location adjacent to an aneurysm having a perforator vessel extending therefrom, a vascular device having a body in a first, collapsed configuration with the body comprising braided strands forming pores and apertures between the strands, the apertures disposed at a longitudinally central portion of the body and separated from one another around a circumference of the body by pores; and
    expanding the body from the first, collapsed configuration to a second, expanded configuration, wherein the apertures are larger than the pores in the second, expanded configuration, at least one aperture aligned with an ostium of the aneurysm such that blood flows through the aneurysm and into the perforator vessel preferentially through the at least one aperture compared to the pores.

17. The method of claim 16, wherein in the first, collapsed configuration, the apertures and pores are substantially the same size as each other.

18. The method of claim 16, wherein the apertures comprises four apertures.

19. The method of claim 16, wherein, in the second, expanded configuration, the apertures are equally spaced and radially arranged around a longitudinal axis of the body.

20. The method of claim 16,
    wherein, in the second, expanded configuration, an area of at least one of the apertures is 0.005 square millimeters or larger;

wherein, in the second, expanded configuration, an area of at least one of the pores is 0.01 square millimeters or smaller; and wherein a thickness of each strand is 0.0010 to 0.0014 inches.

\* \* \* \* \*